United States Patent
Nakayama et al.

(10) Patent No.: US 9,365,484 B2
(45) Date of Patent: Jun. 14, 2016

(54) HEXAESTER OF MONO-FORMAL BIS PENTAERYTHRITOL

(71) Applicant: KH Neochem Co., Ltd., Chuo-ku, Tokyo (JP)

(72) Inventors: Shingo Nakayama, Tokyo (JP); Takuya Nishimura, Mie (JP); Toshihiro Inayama, Mie (JP)

(73) Assignee: KH NEOCHEM CO., LTD., Tokyo (JP)

( * ) Notice: Subject to any disclaimer, the term of this patent is extended or adjusted under 35 U.S.C. 154(b) by 0 days.

(21) Appl. No.: 14/438,039

(22) PCT Filed: Oct. 22, 2013

(86) PCT No.: PCT/JP2013/078512
§ 371 (c)(1),
(2) Date: Apr. 23, 2015

(87) PCT Pub. No.: WO2014/065249
PCT Pub. Date: May 1, 2014

(65) Prior Publication Data
US 2015/0291502 A1   Oct. 15, 2015

(30) Foreign Application Priority Data
Oct. 24, 2012   (JP) .................................. 2012-234841

(51) Int. Cl.
| | |
|---|---|
| C09K 5/04 | (2006.01) |
| C07C 55/24 | (2006.01) |
| C10M 105/38 | (2006.01) |
| C10M 171/00 | (2006.01) |
| C09K 5/00 | (2006.01) |
| C07C 69/33 | (2006.01) |

(52) U.S. Cl.
CPC .................. *C07C 55/24* (2013.01); *C07C 69/33* (2013.01); *C09K 5/00* (2013.01); *C09K 5/041* (2013.01); *C09K 5/042* (2013.01); *C09K 5/045* (2013.01); *C10M 105/38* (2013.01); *C10M 171/008* (2013.01); *C10M 2207/2835* (2013.01); *C10N 2220/022* (2013.01); *C10N 2220/028* (2013.01); *C10N 2230/02* (2013.01); *C10N 2230/08* (2013.01); *C10N 2230/10* (2013.01); *C10N 2240/30* (2013.01)

(58) Field of Classification Search
CPC .................................................... C07M 105/38
USPC ....................................................... 508/485
See application file for complete search history.

(56) References Cited

U.S. PATENT DOCUMENTS

| | | | |
|---|---|---|---|
| 2,464,430 A | 3/1949 | Barth et al. | |
| 4,883,902 A * | 11/1989 | Gohbayashi | .......... C07C 69/732 560/75 |
| 2012/0024007 A1 | 2/2012 | Ota et al. | |

FOREIGN PATENT DOCUMENTS

| | | |
|---|---|---|
| CN | 102408936 A | 4/2012 |
| JP | 53-88825 A | 8/1978 |
| JP | 04-072390 A | 3/1992 |
| JP | 2009-79141 A | 4/2009 |
| JP | 2009-79144 A | 4/2009 |
| JP | 2011-195631 A | 10/2011 |
| JP | 2012-31239 A | 2/2012 |
| JP | 4936656 B2 | 3/2012 |
| JP | 2012-102046 A | 5/2012 |

OTHER PUBLICATIONS

International Search Report (PCT/ISA/210) mailed on Dec. 24, 2013, by the Japanese Patent Office as the International Searching Authority for International Application No. PCT/JP2013/078513.
Written Opinion (PCT/ISA/237) mailed on Dec. 24, 2013, by the Japanese Patent Office as the International Searching Authority for International Application No. PCT/JP2013/078513.
International Search Report (PCT/ISA/210) mailed on Jan. 7, 2014, by the Japanese Patent Office as the International Searching Authority for International Application No. PCT/JP2013/078512.
Written Opinion (PCT/ISA/237) mailed on Jan. 7, 2014, by the Japanese Patent Office as the International Searching Authority for International Application No. PCT/JP2013/078512.
"The Tribology," Jul. 1998, pp. 45-47.
R. Hunter et al., "Synthesis of formaldehyde bis(pentaerythritol) acetal (BPMF)", South African Tydskr. Chem., Jul. 1991, pp. 122-124, vol. 44, Issue 4.
Office Action issued by the Chinese Patent Office in corresponding Chinese Patent Application No. 201380055833.1 on Dec. 3, 2015 (5 pages with partial English translation).

* cited by examiner

*Primary Examiner* — John Hardee
(74) *Attorney, Agent, or Firm* — Buchanan, Ingersoll & Rooney PC

(57) ABSTRACT

Provided is hexaester of bispentaerythritol monoformal, which comprises the bispentaerythritol monoformal represented by the following formula (I), and any one of carboxylic acids selected from C8 and C9 branched aliphatic monocarboxylic acids:

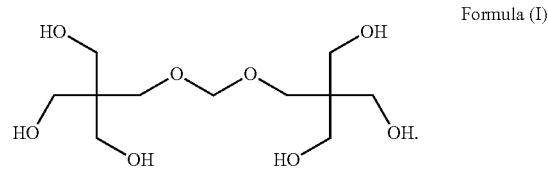

Formula (I)

The hexaester has well-balanced excellent characteristics, such as low temperature properties and oxidation stability, and is used for industrial lubricating oil, such as a refrigerant oil composition.

5 Claims, No Drawings

HEXAESTER OF MONO-FORMAL BIS PENTAERYTHRITOL

TECHNICAL FIELD

The present invention relates to hexaester of bispentaerythritol monoformal, which is used for industrial lubricating oil, such as a refrigerant oil composition.

BACKGROUND ART

Recently, hydrofluorocarbon(s) (HFC) having the ozone depletion potential of 0, and lower global-warming potential (GWP) has been used as a refrigerant for a refrigerator and the like. HFC is a stable refrigerant compared to chlorofluorocarbon(s) (CFC) and hydrochlorofluorocarbon(s) (HCFC), and does not largely affect to lubricant oil, an organic material, and a metal. On the other hand, as HFC does not have sufficient lubricity, the heat generated at a sliding portion accelerates thermal and/or oxidative degradation of refrigerant oil. Therefore, refrigerant oil having high thermal and chemical stability is desired (NPL 1).

And a refrigerant oil is typically circulated together with a refrigerant through part of the refrigeration cycle, and thus the refrigerant oil is exposed to a high temperature range and a low temperature range. In the low temperature range, particularly, part of the refrigerant oil discharged from a compressor may be retained. If the refrigerant oil is exposed in the low temperature range for a long period, the refrigerant oil is crystallized to thereby reduce a circulating amount of the refrigerant in the refrigeration cycle, leading to a cooling failure. Accordingly, it is extremely important to develop refrigerant oil, which is highly stable without precipitating over a long period even in the low temperature range, in view of reliability of a refrigeration device (PTL 1).

PTL 2 describes heat resistance of refrigerant oil containing hexaester which is made by reacting dipentaerythritol with 3,5,5-trimethylhexanoic acid, as a main component. However, the hexaester does not realize low temperature properties, and does not achieve well balanced characteristics required for industrial lubricating oil, such as refrigerant oil.

NPL 2 discloses hexaester which is made by reacting bispentaerythritol monoformal with acetic acid, as an intermediate of bispentaerythritol monoformal, but does not teach or suggest use of the hexaester as industrial lubricating oil, nor low temperature properties or oxidation stability thereof.

CITATION LIST

Patent Literature

PTL 1: Japanese Patent (JP-B) No. 4936656
PTL 2: Japanese Patent Application Laid-Open (JP-A) No. 04-72390

Non-Patent Literature

NPL 1: "The Tribology," 1998, July, p. 45
NPL 2: "South African Journal of Chemistry," 1991, Vol. 44, No. 4, p. 122

SUMMARY OF INVENTION

Technical Problem

An object of the present invention is to provide hexaester of bispentaerythritol monoformal, which has well-balanced excellent characteristics, such as low temperature properties and oxidation stability, and is used for industrial lubricating oil, such as a refrigerant oil composition.

Solution to Problem

The present invention provides the following [1] to [5].
[1] Hexaester of bispentaerythritol monoformal, which comprises the bispentaerythritol monoformal represented by the following formula (I), and any one of carboxylic acids selected from C8 and C9 branched aliphatic monocarboxylic acids:

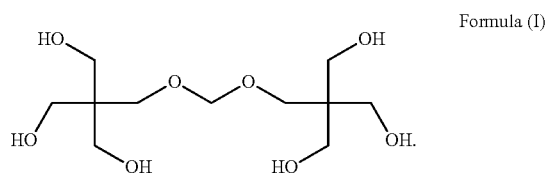 [SMILES: OCC(CO)(CO)COCOCC(CO)(CO)CO]

Formula (I)

[2] The hexaester of bispentaerythritol monoformal according to [1], wherein the carboxylic acid is C9 branched aliphatic monocarboxylic acid.
[3] The hexaester of bispentaerythritol monoformal according to [1], wherein the carboxylic acid is 3,5,5-trimethylhexanoic acid.
[4] A refrigerant oil composition, comprising:
    the hexaester of bispentaerythritol monoformal according to any one of [1] to [3].
[5] A working fluid composition for refrigerators, comprising:
    the refrigerant oil composition according to [4]; and
    a refrigerant.

Advantageous Effects of Invention

The present invention can provide hexaester of bispentaerythritol monoformal, which has well-balanced excellent characteristics, such as low temperature properties and oxidation stability, and is used for industrial lubricating oil, such as a refrigerant oil composition.

DESCRIPTION OF EMBODIMENTS

The hexaester of the present invention is hexaester of bispentaerythritol monoformal, which comprises the bispentaerythritol monoformal represented by the following formula (I), and any one of carboxylic acids selected from C8 and C9 branched aliphatic monocarboxylic acids:

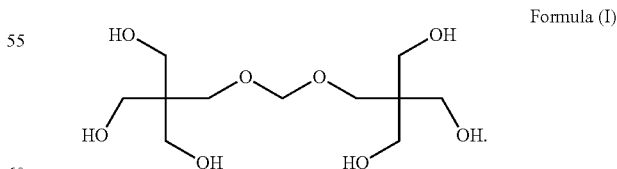

Formula (I)

The hexaester of bispentaerythritol monoformal of the present invention may contain, as impurities, a partial ester of the bispentaerythritol monoformal, in which part of hydroxyl groups are remained without being esterified.

Examples of the carboxylic acid constituting the hexaester of bispentaerythritol monoformal, which is selected from C8 and C9 branched aliphatic monocarboxylic acids, include 2-methylheptanoic acid, 2-ethylhexanoic acid, 3-ethylhexanoic acid, 2-ethyl-2-methylpentanoic acid, 2-ethyl-4-methylpentanoic acid, 2-methyloctanoic acid, 2,2,-dimethylheptanoic acid, and 3,5,5-trimethylhexanoic acid. Among them, preferred is C9 branched aliphatic monocarboxylic acid, such as 2-methyloctanoic acid, 2,2-dimethylheptanoic acid, and 3,5,5-trimethylhexanoic acid, and more preferred is 3,5,5-trimethylhexanoic acid, in view of oxidation stability thereof.

Bispentaerythritol monoformal constituting the hexaester of bispentaerythritol monoformal according to the invention may be produced in accordance with the method disclosed in NPL2: by triacetylating pentaerythritol with acetic anhydride, condensing the obtained pentaerythritol triacetate with dimethoxy methane in the presence of an acid catalyst, and carrying out hydrolysis of acetyl groups of the obtained condensate. Moreover, the bispentaerythritol monoformal can be obtained in accordance with the method (e.g., the method disclosed in U.S. Pat. No. 2,464,430): by allowing acetaldehyde and formaldehyde to react with each other in the presence of a base to produce pentaerythritol, and extracting bispentaerythritol monoformal generated in the process of the reaction as a by-product using butyl acetate. As for another method, the bispentaerythritol monoformal can be obtained by allowing pentaerythritol and 1,1,1-trimethoxyethane to react with each other to obtain a compound (the below-described compound (i)), allowing the obtained compound and dibromomethane to react with each other in the presence of a base to obtain a compound (the below-described compound (ii)), and carrying out hydrolysis of orthoester groups of the obtained compound (the compound (ii)), as described in Production Example 1, which is described later.

The hexaester of bispentaerythritol monoformal of the present invention can be produced, for example, by allowing bispentaerythritol monoformal and any one of carboxylic acids selected from C8 and C9 branched aliphatic monocarboxylic acids with each other for 5 hours to 60 hours at 120° C. to 300° C. (this method is referred to as the production method 1, hereinafter).

Catalyst(s) may be used in the production method 1. Examples of the catalyst include mineral acids, organic acids, Lewis acids, organic metals, and solid acids. Specific examples of the mineral acid include hydrochloric acid, hydrofluoric acid, sulfuric acid, phosphoric acid, nitric acid, and the like. Specific examples of the organic acid include p-toluenesulfonic acid, benzenesulfonic acid, butanesulfonic acid, propanesulfonic acid, ethanesulfonic acid, methanesulfonic acid, and the like. Specific examples of the Lewis acid include boron trifluoride, aluminium chloride, tin tetrachloride, titanium tetrachloride, and the like. Specific examples of the organic metal include tetrapropoxy titanium, tetrabutoxy titanium, tetrakis(2-ethylhexyloxy)titanium, and the like. Examples of the solid acid include a cation-exchange resin and the like.

In the production method 1, it is preferred that the reaction be carried out with removing the water produced during the reaction from the reaction mixture. Moreover, an amount of the carboxylic acid for use, which is selected from C8 and C9 branched aliphatic monocarboxylic acids, is preferably 1.1 mol to 1.4 mol relative to 1 mol of hydroxyl groups of the bispentaerythritol monoformal.

Moreover, the hexaester of bispentaerythritol monoformal of the present invention can be produced, for example, by allowing bispentaerythritol and an anhydride of the carboxylic acid selected from C8 and C9 branched aliphatic monocarboxylic acids to react with each other for 1 hour to 10 hours at 50° C. to 100° C. (this method is referred to as the production method 2, hereinafter).

Catalyst(s) may be used in the production method 2. Examples of the catalyst include organic bases, organic salts, and solid acids. Specific examples of the organic base include pyridine, N,N-dimethyl-4-aminopyridine, and the like. Specific examples of the organic salt include sodium acetate, scandium (III) trifluoromethanesulfonyl imide, trimethylsilyl trifluoromethanesulfonate, and the like. Specific examples of the solid acid include a cation-exchange resin and the like.

In the production example 2, an amount of the anhydride of the carboxylic acid for use, which is selected from C8 and C9 branched aliphatic monocarboxylic acids is preferably 0.5 mol to 1.4 mol relative to 1 mol of hydroxyl groups of the bispentaerythritol monoformal.

Solvent(s) may be used in the production methods 1 and 2. Examples of the solvent include hydrocarbon-based solvents, such as benzene, toluene, xylene, hexane, heptane, isohexane, isooctane, isononane, decane, and the like.

In the production methods 1 and 2, the hexaester of bispentaerythritol monoformal of the present invention may be optionally purified after the reaction by a method typically used in synthetic organic chemistry (e.g., washing with water and/or an alkali aqueous solution, treatment with an activated carbon, an adsorbent, and the like, various chromatography, and distillation).

The hexaester of bispentaerythritol monoformal of the present invention has excellent low temperature properties, excellent oxidation stability, and sufficient thermal stability. Moreover, the hexaester of bispentaerythritol of the present invention is easily produced, as one type of the carboxylic acid is used for constituting the hexaester. Therefore, there is an advantage that a quality thereof is stabilized.

The hexaester of bispentaerythritol monoformal of the present invention, especially hexaester which is made by reacting bispentaerythritol monoformal with 3,5,5-trimethylhexanoic acid, has excellent characteristics, such as low temperature properties, and oxidation stability, with a desired balance. Moreover, the hexaester has extremely excellent oxidation stability compared to a conventional base oil for a refrigerant oil (e.g., a mixture of esters which is made by reacting pentaerythritol, 2-ethylhexanoic acid, and 3,5,5-trimethylhexanoic acid).

When the hexaester of bispentaerythritol monoformal of the present invention is used in a refrigerant oil composition, the refrigerant oil composition is clouded at low temperature, if an amount of hydroxyl groups in the hexaester is large. The clouding of the refrigerant oil composition causes an undesirable phenomenon, such as a clogging of a capillary device of a refrigeration cycle. Therefore, a hydroxyl number of the hexaester is preferably 20 mgKOH/g or lower, more preferably 10 mgKOH/g or lower.

The refrigerant oil composition of the present invention is a refrigerant oil composition containing the hexaester of bispentaerythritol monoformal of the present invention. For example, the refrigerant oil composition is composed of only the hexaester, or composed of the hexaester and another base oil for a refrigerant oil.

The hexaester of bispentaerythritol monoformal of the present invention is determined by an analysis method, such as nuclear magnetic resonance (which is referred to as NMR hereinafter), gas chromatography (which is referred to as GC hereinafter), and gas chromatography-mass spectrometry (which is referred to as GC-MS hereinafter). In the refrigerant oil composition of the present invention, the hexaester of bispentaerythritol monoformal of the present invention contained in the refrigerant oil composition is determined by the similar analysis methods. Optionally, the hexaester bispentaerythritol monoformal is separated from the refrigerant oil composition in advance by a method, such as column chromatography, distillation, a solvent extraction, crystallization, and the like. In this manner, the determination can be performed easily.

Examples of another base oil for a refrigerant oil for use in the refrigerant oil composition of the present invention include mineral oil, and synthetic base oil.

Examples of the mineral oil include paraffinic-base crude oil, intermediate-base crude oil, naphthenic-base crude oil, and the like. Moreover, refined oil, obtained by refining any of the above-listed oil via distillation and the like, may also be used.

Examples of the synthetic base oil include poly-α-olefin (e.g., polybutene, polypropylene, and α-olefin oligomers having 8 to 14 carbon atoms), aliphatic esters other than the hexaester of bispentaerythritol monoformal of the present invention (e.g., fatty acid monoesters, fatty acid esters of polyhydric alcohols, and aliphatic polybasic acid esters), aromatic esters (e.g., aromatic monoesters, aromatic esters of polyhydric alcohols, and aromatic polybasic acid esters), polyalkylene glycols, polyvinyl ethers, polycarbonates, alkyl benzenes, and the like. Examples of the polyhydric alcohol include hindered alcohols, such as pentaerythritol, polypentaerythritol (e.g., a condensate of pentaerythritol, such as dipentaerythritol, tripentaerythritol, and tetrapentaerythritol), neopentyl glycol, trimethylol propane, and the like.

An amount of the another base oil for a refrigerant oil is not particularly limited, as long as it does not adversely affect various characteristics, such as low temperature properties, and oxidation stability.

The refrigerant oil composition of the present invention may optionally further comprise lubricant additive(s). Examples of the lubricant additive include a metal deactivator, an antioxidant, a wear-reducing agent (e.g., an anti-wear agent, an anti-seizure agent, and an extreme-pressure agent), a friction modifier, an acid scavenger, a rust preventative agent, an anti-foaming agent, and the like. The content of each additive in the refrigerant oil composition is preferably 0.001 weight % to 5 weight %.

The refrigerant oil composition of the present invention has excellent characteristics, such as low temperature properties, and oxidation stability, as the refrigerant oil composition contains the hexaester of bispentaerythritol monoformal.

The refrigerant oil composition is used for a refrigeration system of a domestic air conditioner. However, there is a case where air is included in a refrigeration cycle when the refrigeration system is installed, and thus the refrigerant oil composition is influenced by oxygen. Therefore, the refrigerant oil composition requires high oxidation stability.

The oxidation stability of the hexaester of bispentaerythritol monoformal of the present invention, and the refrigerant oil composition of the present invention can be evaluated by measuring RBOT life by an oxidation stability test. In the present specification, the RBOT life is measured by the method described in the test example, which is described later.

And in the case the refrigerant oil composition is stored for a long period or used at a place having a significant temperature change, the refrigerant oil composition is preferably not volatile at the high temperature range, and is not preferably solidified or precipitated at the low temperature range. The temperature range is not particularly limited, but the refrigerant oil composition is preferably stably used at around 150° C. for the high temperature range, and at around −20° C. for the low temperature range. In the present specification, the properties of the oil composition, which is not solidified or precipitated at the low temperature range, are determined as low temperature properties. The low temperature properties are typically influenced by a chemical structure of the hexaester. For example, an ester formed from a single type of carboxylic acid, the ester tends to be crystallized, and therefore if the ester used as the refrigerant oil, a circulating amount of a refrigerant of the refrigeration system tends to reduce. However, the hexaester of bispentaerythritol monoformal of the present invention has excellent low temperature properties, even through a single type of the carboxylic acid is used for constituting the hexaester.

The working fluid composition for refrigerators of the present invention is a composition containing the refrigerant oil composition of the present invention and a refrigerant. The hexaester of bispentaerythritol monoformal of the present invention is used for the refrigerant oil composition of the working fluid composition for refrigerators. A blending ratio of the hexaester of bispentaerythritol monoformal of the present invention and the refrigerant is not particularly limited, but the hexaester of bispentaerythritol monoformal of the present invention is preferably 1 part by weight to 1,000 parts by weight, more preferably 2 parts by weight to 800 parts by weight, relative to 100 parts by weight of the refrigerant.

Examples of the refrigerant of the working fluid composition for refrigerators include a fluorine-containing refrigerant, a natural refrigerant, and the like.

Examples of the fluorine-containing refrigerant include: hydrofluorocarbon, such as difluoromethane (HFC32), trifluoromethane (HFC23), pentafluoroethane (HFC125), 1,1,2,2-tetrafluoroethane (HFC134), 1,1,1,2-tetrafluoroethane (HFC134a), 1,1,1-trifluoroethane (HFC143a); unsaturated fluorohydrocarbon, such as 2,3,3,3-tetrafluoropropene (HFO1234yf), 1,3,3,3-tetrafluoropropene (HFO1234ze), 1,2,3,3-tetrafluoropropene (HFO1234ye), and 1,2,3,3,3-pentafluoropropene (HFO1225ye); and a mixture thereof.

Examples of the natural refrigerant include hydrocarbon (e.g., propane, butane, and isobutane), carbon dioxide, ammonia, and the like.

Other than a refrigerant oil composition and a working fluid composition for refrigerators, the hexaester of bispentaerythritol monoformal of the present invention can be used for engine oil, gear oil, motor oil used for hybrid cars or electric cars, grease, additives for lubricant oil, a detergent of metal parts, a plasticizer, a cosmetic product, and the like. Moreover, the refrigerant oil composition and the working fluid composition for refrigerators of the present invention are suitably used for domestic air conditioners, packaged air conditioners, automotive air conditioners, dehumidifiers, refrigerators, freezers, fridge-freezers, vending machines, display cases, or refrigeration systems of chemical plants.

EXAMPLES

The present invention is more specifically explained through production examples, examples, comparative examples, and test examples, hereinafter. However, the invention is not limited to the following examples.
<NMR>

The bispentaerythritol monoformal and esters obtained in Production Example 1, Example 1, and Example 2 were measured by NMR. The NMR measurement was performed by means of the following measuring device, and in the following measurement method.

Measuring device; GSX-400 (400 MHz) (manufactured by JOEL Ltd.)
Measurement Method;
Nucleus type: $^1$H
Reference standard; tetramethylsilane
Solvent; CDCl$_3$ or d$_6$-DMSO

<GC>

The purity of the bispentaerythritol monoformal obtained in Production Example 1 below was measured by GC. The GC measurement was performed by means of the following measuring device under the following measuring conditions, after preparing a test liquid in the following method.

Preparation method of test liquid; A reactor was charged with 10 mg of the bispentaerythritol monoformal obtained in Production Example 1 below, and 1 mL of a trimethylsilylating agent (product name: TMS-HT, manufactured by Tokyo Chemical Industry Co., Ltd.), and the resulting mixture was stirred for 10 minutes at 80° C. After the reaction was completed, the reaction liquid was filtered with a membrane filter (PTFE, 0.5 μm). The resulting filtrate was provided as a test liquid.

Measuring device: Agilent 7890A (manufactured by Agilent Technologies, Inc.)
Measuring Conditions:
Column: HP-5 (length: 30 m, I.D.: 0.320 mm, film thickness: 0.25 μm) (manufactured by Agilent Technologies, Inc.)
Carrier gas: nitrogen, flow rate 1.0 mL/min
INJ/DET temperature: 330° C./350° C.
Injection mode: split mode (1 μL injection, split ratio: 1/50)
Detector: FID
Temperature program: start with an initial temperature of 100° C., a ramp rate of 10° C./min, a final temperature of 325° C., and a final hold time of 17.5 min.

<GC-MS>

The esters obtained in Examples 1 and 2 below were measured by GC-MS.

The GC-MS measurement was performed by means of the following measuring device under the following measuring conditions.

Measuring devices: Agilent 7890A (manufactured by Agilent Technologies, Inc.)
JOEL JMS-T100GC$_v$ mass spectrometer (manufactured by JOEL Ltd.)
Measuring Conditions:
Column: DB-5 (length: 30 m, I.D.: 0.25 mm, film thickness: 0.25 μm) (manufactured by Agilent Technologies, Inc.)
Carrier gas: helium, flow rate 1.0 mL/min
Injection temperature: 300° C.
Injection mode: split mode (split ratio: 1/50)
Ionization method: CI (reagent gas; ammonia), EI
Temperature program: start with an initial temperature of 100° C., a ramp rate of 10° C./min, a final temperature of 325° C., and a final hold time of 97.5 min.

<High Performance Liquid Chromatography>

The purity of the bispentaerythritol monoformal obtained in Production Example 1 below was measured by high performance liquid chromatography (referred to as LC, hereinafter). The LC measurement was performed by means of the following measuring device under the following measuring conditions, after preparing a test liquid by the following method.

Preparation method of test liquid; A test liquid was prepared by blending 2.5 mg of the bispentaerythritol monoformal obtained in Production Example 1 below, and 497.5 mg of 0.1 weight % phosphoric acid aqueous solution.

Measuring device: Agilent 1200 Series (manufactured by Agilent Technologies, Inc.)
Measuring Conditions:
Column: YMC-Pack ODS-AM (spherical particle, particle size: 5 μm, pore size: 12 nm, length: 300 mm, I.D.: 4.6 mm) (manufactured by YMC CO., LTD.)
Solvent: 0.1 weight % phosphoric acid aqueous solution, flow rate 0.7 mL/min
Column temperature: 40° C.
Injection volume of sample: 5 μL
Detector: RI Production Example 1

Production of Bispentaerythritol Monoformal (1) Production of Compound (i)

Compound (i)

A reactor equipped with a Dean-Stark trap was charged with 544.6 g of pentaerythritol (4.00 mol, product name: Pentarit-S, manufactured by Koei Chemical Company, Limited), 480.6 g of 1,1,1-trimethoxyethane (4.00 mol, manufactured by Tokyo Chemical Industry Co., Ltd.), 6.9 g of p-toluenesulfonic acid monohydrate (0.04 mol, manufactured by Tokyo Chemical Industry Co., Ltd.), and 2 L of toluene, and the mixture was stirred for 14 hours at 70° C. to 100° C. The Dean-Stark trap was replaced with a dropping funnel filled with molecular sieves, followed by stirring the mixture for 10 hours at 110° C. to 120° C. After completing the reaction, the reaction product was condensed, and 20.4 g of triethylamine was added to the resulting condensed product. The resultant was then crystallized with 2.6 L of dichloromethane, to thereby yield 234.6 g of a compound (i).

$^1$H-NMR (CDCl$_3$, δ ppm); 1.46 (s, 3H), 3.47 (s, 2H), 4.02 (s, 6H)

(2) Production of Compound (ii)

Compound (ii)

A reactor was charged with 72.8 g of sodium hydride dispersed in liquid paraffin (concentration of sodium hydride: 60 weight %, manufactured by Tokyo Chemical Industry Co., Ltd.), 224.2 g of the compound (i), and 3.5 L of dimethylformamide. To this, 121.7 g of dibromomethane (0.70 mol, manufactured by Tokyo Chemical Industry Co., Ltd.) was dropped at 0° C. The resulting mixture was stirred for 1 hour at room temperature, followed by adding 130 mL of methanol. After completing the reaction, the reaction product was condensed at 70° C. under the reduced pressure of 1.3 kPa. The condensed product was diluted with 2.5 L of dichloromethane, and then washed with 1 L of water. The organic layer was condensed, and the condensed product was crystallized with 10.6 L of methanol, to thereby yield 62.7 g of a compound (ii).

$^1$H-NMR (CDCl$_3$, δ ppm): 1.46 (s, 6H), 3.24 (s, 4H), 3.98 (s, 12H), 4.53 (s, 2H)

(3) Production of Bispentaerythritol Monoformal

A reactor was charged with 78.3 g of the compound (ii), and 320 g of water, and the resulting mixture was stirred for 2 hours at 100° C. Subsequently, 1905.0 g of a strong-base anion exchange resin (product name: DIAION SA11A, manufactured by Mitsubishi Chemical Corporation) was added to the mixture, and the resultant was stirred for 1 hour at room temperature. The reaction product was filtered, followed by condensing the filtrate. The condensed product was crystallized with 1.7 L of ethanol, to thereby yield 53.6 g of bispentaerythritol monoformal.

$^1$H-NMR (d$_6$-DMSO, δ ppm); 3.32-3.40 (m, 16H), 4.25 (t, 6H), 4.54 (s, 2H)

The purity measured by GC: 95 area % or greater
The purity measured by LC: 95 area % or greater Production Example 2

Production of 3,5,5-Trimethylhexanoic Anhydride

A reactor was charged with 633.0 g of 3,5,5-trimethylhexanoic acid (4.00 mol, manufactured by KH Neochem Co., Ltd.) and 817.5 g of acetic anhydride (8.00 mol, manufactured by Wako Pure Chemical Industries, Ltd.), and the resulting mixture was stirred for 1 hour at 120° C. After completing the reaction, the reaction product was distilled at 157° C. to 162° C. under the reduced pressure of 0.4 kPa, to thereby yield 496.4 g of 3,5,5-trimethylhexanoic anhydride.

Production Example 3

Production of 2-Ethylhexanoic Anhydride

A reactor was charged with 721.1 g of 2-ethylhexanoic acid (5.00 mol, manufactured by KH Neochem Co., Ltd.) and 919.7 g of acetic anhydride (9.00 mol, manufactured by Wako Pure Chemical Industries, Ltd.), and the resulting mixture was stirred for 1 hour at 120° C. After completing the reaction, the reaction product was distilled at 126° C. to 133° C. under the reduced pressure of 0.1 kPa, to thereby yield 509.8 g of 2-ethylhexanoic anhydride.

Example 1

Production of Hexaester of Bispentaerythritol Monoformal and 3,5,5-Trimethylhexanoic Acid (Hexaester 1)

A reactor was charged with 11.4 g (0.04 mol) of the bispentaerythritol monoformal produced in Production Example 1, 86.0 g (0.29 mol) of the 3,5,5-trimethylhexanoic anhydride produced in Production Example 2, and 38.0 g of pyridine (0.48 mol, manufactured by Wako Pure Chemical Industries, Ltd.), and the resulting mixture was degassed by nitrogen bubbling for 15 minutes at room temperature under the reduced pressure of 20 kPa. Subsequently, the mixture, which had been subjected to degassing, was stirred for 5 hours at 70° C. to 100° C. with nitrogen bubbling. After completing the reaction, the reaction product was condensed for 1 hour at 150° C. to 220° C. under the reduced pressure of 1.3 kPa. The condensed product was washed once with 30 mL of an alkaline aqueous solution containing 2 fold moles of sodium hydroxide relative to the acid number of the condensed product, followed by washing three times with 30 mL of water. Then, the resultant was dehydrated for 1 hour at 110° C. under the reduced pressure of 1.3 kPa with nitrogen bubbling. Subsequently, 0.23 g of an adsorbent (product name: KYOWAAD 500, manufactured by Kyowa Chemical Industry Co., Ltd.), and 0.45 g of activated carbon (product name: SHIRASAGI P, manufactured by Japan EnviroChemicals, Ltd.) were added, and the resultant was stirred for 1 hour at 110° C. under the reduced pressure of 1.3 kPa with nitrogen bubbling. Subsequently, the resultant was filtered with a membrane filter (PTFE, 0.2 μm), to thereby yield 38.2 g of Hexaester 1.

$^1$H-NMR (CDCl$_3$, δ ppm); 0.90 (s, 54H), 0.97 (d, 18H), 1.08-1.16 (m, 6H), 1.19-1.27 (m, 6H), 1.97-2.07 (m, 6H), 2.09-2.18 (m, 6H), 2.28-2.36 (m, 6H), 3.51 (s, 4H), 4.11 (s, 12H), 4.57 (s, 2H)
GC-MS (Cl): m/z (molecule ion) 1143 ([M+NH$_4$]$^+$)
GC-MS (El): m/z (fragment ion) 141, 539

Example 2

Production of Hexaester of Bispentaerythritol Monoformal and 2-Ethylhexanoic Acid (Hexaester 2)

Hexaester 2 was obtained in the same manner as in Example 1, except that the 3,5,5-trimethylhexanoic anhydride was replaced with the 2-ethylhexanoic anhydride produced in Production Example 3.

$^1$H-NMR (CDCl$_3$, δ ppm); 0.70-0.95 (m, 36H), 1.10-1.37 (m, 24H), 1.37-1.70 (m, 24H), 2.17-2.35 (m, 6H), 3.53 (s, 4H), 4.11 (s, 12H), 4.58 (s, 2H)
GC-MS (Cl): m/z (molecule ion) 1059 ([M+NH$_4$]$^+$)
GC-MS (El): m/z (fragment ion) 127, 497

Comparative Example 1

Production of Hexaester of Dipentaerythritol and 3,5,5-Trimethylhexanoic Acid (Hexaester A)

A reactor equipped with a Dean-Stark trap was charged with 63.6 g of dipentaerythritol (0.25 mol, product name: Dipentarit, manufactured by Koei Chemical Company, Limited), and 347.0 g of 3,5,5-trimethylhexanoic acid (2.20 mol, manufactured by KH Neochem Co., Ltd.), and the resulting mixture was degassed by nitrogen bubbling for 30 minutes at room temperature under the reduced pressure of 20 kPa. Subsequently, the mixture, which had been subjected degassing, was stirred for 10.5 hours at 170° C. to 230° C. with nitrogen bubbling. After completing the reaction, the reaction product was condensed for 2.5 hours at 120° C. to 220° C. under the reduced pressure of 1.2 kPa. The condensed product was diluted with hexane, and the resultant was washed once with 90 mL of an alkaline aqueous solution containing 2 fold moles of sodium hydroxide relative to the acid number of the condensed product, followed by washing twice with 90 mL of water. The resulting organic layer was dehydrated for 1.5 hours at 100° C. under the reduced pressure of 1.3 kPa with nitrogen bubbling. Subsequently, 2.7 g of an adsorbent (product name: KYOWAAD 500, manufactured by Kyowa Chemical Industry Co., Ltd.), and 5.5 g of activated carbon (product name: SHIRASAGI P, manufactured by Japan EnviroChemicals, Ltd.) were added, and the resultant was stirred for 1 hour at 100° C. under the reduced pressure of 1.3 kPa. Subsequently, the resultant was filtered with a filter aid (product name: Radiolite #500, manufactured by Showa Chemical Industry Co., Ltd.), to thereby yield 213.1 g of Hexaester A.

Comparative Example 2

Production of Hexaester of Bispentaerythritol Monoformal and Acetic Acid (Hexaester B)

Hexaester B was obtained in the same manner as in Example 1, except that the 3,5,5-trimethylhexanoic anhydride was replaced with acetic anhydride (manufactured by Wako Pure Chemical Industries, Ltd.).

Test Example 1

Measurement of Kinematic Viscosity of Hexaester

The kinematic viscosity of Hexaester 1, Hexaester 2, Hexaester A, and Hexaester B at 40° C. and 100° C. was measured by means of Cannon-Fenske Viscometer in accordance with the method of JIS K2283:2000. The results are presented in Table 1.

Test Example 2

Evaluation of Low Temperature Properties of Hexaester (Confirmation of Presence of Solidification and Precipitation at −20° C.)

1 g of hexaester (Hexaester 1, Hexaester 2, Hexaester A, and Hexaester B) was placed in a glass container, and was left to stand for 24 hours in a thermostat container set to −20° C. After leaving to stand for 24 hours, the presence of solidification and precipitation was confirmed visually. The case where no solidification or precipitation was confirmed was determined as I, and the case where solidification or precipitation was confirmed was determined as II. The results are presented in Table 1.

Test Example 3

Evaluation of Oxidation Stability of Hexaester (Measurement of RBOT Life)

An oxidation stability test was performed by means of a rotating bomb oxidation tester RBOT-02 (manufactured by Rigo Co., Ltd.). 10 g of hexaester (Hexaester 1, Hexaester 2, Hexaester A, and Hexaester B) and electrolytic copper wire (diameter: 1.6 mm, length: 3 m) polished with sand paper #400 were placed in a pressure vessel. Subsequently, oxygen was introduced into the pressure vessel until the pressure reached 620 kPa. The pressure vessel was placed in a thermostat bath set to 150° C., and a test was initiated by rotating the pressure vessel at 100 rpm, which was recorded as the starting point of the test. The point where the pressure was declined by 35 kPa from the maximum pressure reached by the pressure vessel was determined as a terminal point. The time from the starting point of the test to the terminal point (RBOT life) was determined. The results are presented in Table 1. The longer the RBOT life is more excellent oxidation stability the hexaester has.

Test Example 4

Evaluation of Thermal Stability of Hexaester (Measurement of Weight Loss Temperature)

The 5% weight loss temperature of each of Hexaester 1 and Hexaester 2 was measured by means of a thermogravimetry and differential thermal analyzer TG/DTA6200 (manufactured by Seiko Instruments Inc.) under the following measuring conditions. The results are presented below.
Measuring Conditions;
Measuring temperature: 40° C. to 420° C.
Temperature ramp rate: 10° C./min
Atmosphere: nitrogen flow (300 mL/min)
Sample container: aluminium container 15 μl (open)
Sample amount: 3 mg

TABLE 1

| | | Hexaester 1 (Ex. 1) | Hexaester 2 (Ex. 2) | Hexaester A (Comp. Ex. 1) | Hexaester B (Comp. Ex. 2) |
|---|---|---|---|---|---|
| Alcohol | | BPE | BPE | DPE | BPE |
| Carboxylic acid | | iC9 acid | 2EH acid | iC9 acid | Acetic acid |
| Kinematic viscosity ($mm^2/sec$) | 40° C. | 487 | 168 | 403 | solid |
| | 100° C. | 28.4 | 15.4 | 26.2 | 17.5 |
| Low temperature properties | | I | I | II | II |
| RBOT life (min) | | 260 | 60 | 168 | 30 |

*BPE: bispentaerythritol monoformal
*DPE: dipentaerythritol
*iC9 acid: 3,5,5-trimethylhexanoic acid
*2EH acid: 2-ethylhexanoic acid It was confirmed from Table 1 that Hexaester 1 and Hexaester 2 were not solidified or precipitated at −20° C., and exhibited excellent low temperature properties. Moreover, the RBOT life of Hexaester 1 was 260 minutes, and the RBOT life of Hexaester 2 was 60 minutes. Hexaester 1 had the RBOT life 4 times or longer the RBOT life of Hexaester 2, and thus exhibited extremely excellent oxidation stability. This result is a surprising result that cannot be expected from the structure of carboxylic acid constituting the hexaester. It can be seen that Hexaester 1 and Hexaester 2 have excellent low temperature properties and oxidation stability in a well-balanced manner. On the other hand, Hexaester A and Hexaester B had undesirable low temperature properties, and Hexaester B had poor oxidation stability, and thus Hexaester A and Hexaester B did not have well-balanced properties. Moreover, Hexaester B was crystallized at 40° C. Therefore, Hexaester B cannot be used as industrial lubricant oil, such as a refrigerant oil composition at all.

In Test Example 4, the 5% weight loss temperature of Hexaester 1 and that of Hexaester 2 were both 247° C. or higher. Therefore, it can be understood that Hexaester 1 and Hexaester 2 have sufficient thermal stability.

INDUSTRIAL APPLICABILITY

The present invention can provide hexaester of bispentaerythritol monoformal, which has well-balanced excellent characteristics, such as low temperature properties and oxidation stability, and is used for industrial lubrication oil, such as a refrigerant oil composition.

The invention claimed is:

1. Hexaester of bispentaerythritol monoformal, which comprises the bispentaerythritol monoformal represented by the following formula (I), and any one of carboxylic acids selected from C8 and C9 branched aliphatic monocarboxylic acids:

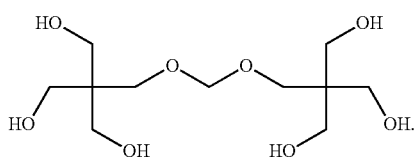

Formula (I)

2. The hexaester of bispentaerythritol monoformal according to claim 1, wherein the carboxylic acid is C9 branched aliphatic monocarboxylic acid.

3. The hexaester of bispentaerythritol monoformal according to claim 1, wherein the carboxylic acid is 3,5,5-trimethylhexanoic acid.

4. A refrigerant oil composition, comprising:
hexaester of bispentaerythritol monoformal,
wherein the hexaester of bispentaerythritol monoformal comprises the bispentaerythritol monoformal represented by the following formula (I), and any one of carboxylic acids selected from C8 and C9 branched aliphatic monocarboxylic acids:

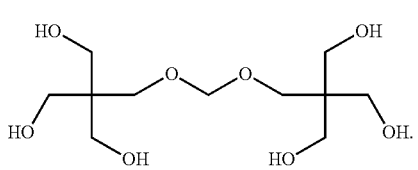

Formula (I)

5. A working fluid composition for refrigerators, comprising:
a refrigerant oil composition; and
a refrigerant,
wherein the refrigerant oil composition comprises hexaester of bispentaerythritol monoformal, and
wherein the hexaester of bispentaerythritol monoformal comprises the bispentaerythritol monoformal represented by the following any one of carboxylic acids selected from C8 and C9 branched aliphatic monocarboxylic acids:

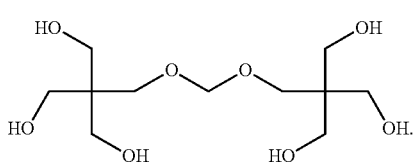

Formula (I)

* * * * *